United States Patent
Kohli et al.

(10) Patent No.: US 8,871,454 B2
(45) Date of Patent: Oct. 28, 2014

(54) BIOMARKERS AND METHODS FOR DETERMINING DISEASE PROGRESSION IN NONALCOHOLIC STEATOHEPATITIS (NASH)

(75) Inventors: Rohit Kohli, Mason, OH (US); Stavra A. Xanthakos, Cincinnati, OH (US); Michael V. Miles, Mason, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 666 days.

(21) Appl. No.: 13/014,580

(22) Filed: Jan. 26, 2011

(65) Prior Publication Data

US 2011/0212468 A1    Sep. 1, 2011

Related U.S. Application Data

(60) Provisional application No. 61/298,409, filed on Jan. 26, 2010.

(51) Int. Cl.
*G01N 33/53* (2006.01)
*G01N 31/00* (2006.01)
*G01N 33/573* (2006.01)

(52) U.S. Cl.
CPC ...... *G01N 33/5735* (2013.01); *G01N 2800/085* (2013.01)
USPC ........... 435/7.21; 435/7.1; 436/501; 436/518; 424/9.1; 424/520; 422/430; 530/300; 530/350

(58) Field of Classification Search
CPC . A61K 2300/00; A61K 45/06; A61K 31/522; G01N 2800/085
See application file for complete search history.

(56) References Cited

PUBLICATIONS

Baumgardner JN et al., A new model for nonalcoholic steatohepatitis in the rat utilizing total enteral nutrition to overfeed a high-polyunsaturated fat diet. *Am J Physiol Gastrointest Liver Physiol* 2008; 294:G27-38.

Bray GA et al., Consumption of high-fructose corn syrup in beverages may play a role in the epidemic of obesity. *Am J Clin Nutr* 2004; 79:537-543.

Cave M et al., Nonalcoholic fatty liver disease: predisposing factors and the role of nutrition. *J Nutr Biochem* 2007; 18:184-195.

George J et al., Lipid peroxidation, stellate cell activation and hepatic fibrogenesis in a rat model of chronic steatohepatitis. *J Hepatol* 2003; 39:756-764.

Leclercq IA et al., CYP2E1 and CYP4A as microsomal catalysts of lipid peroxides in murine nonalcoholic steatohepatitis. *J Clin Invest* 2000; 105:1067-1075.

Oben JA, et al., Norepinephrine induces hepatic fibrogenesis in leptin deficient ob/ob mice.*Biochem Biophys Res Commun* 2003; 308:284-292.

Rinella ME et al., Mechanisms of hepatic steatosis in mice fed a lipogenic methionine choline deficient diet. *J Lipid Res* 2008; 49:1068-1076.

Sahai A et al., Upregulation of osteopontin expression is involved in the development of nonalcoholic steatohepatitis in a dietary murine model. *Am J Physiol Gastrointest Liver Physiol* 2004; 287:G264-273.

Saxena NK et al., Leptin in hepatic fibrosis: evidence for increased collagen production in stellate cells and lean littermates of ob/ob mice. *Hepatology* 2002; 35: 762-771.

Watanabe S et al., Hepatocyte-specific Pten-deficient mice as a novel model for nonalcoholic steatohepatitis and hepatocellular carcinoma. *Hepatol Res* 2005; 33:161-166.

*Primary Examiner* — Lisa Cook
(74) *Attorney, Agent, or Firm* — Knobbe Martens Olson & Bear LLP

(57) ABSTRACT

Diets high in saturated fat and fructose have been implicated in the development of obesity and nonalcoholic steatohepatitis (NASH) in humans. Provided herein are biomarkers, methods, and animal models useful for the investigation and non-invasive detection of NASH, including a non-invasive biomarker that could be used to establish disease severity, follow progression, and evaluate response to treatment in clinical trials for this increasingly prevalent disease.

47 Claims, 14 Drawing Sheets

← 0.04%

← 0.03%

BIOMARKERS AND METHODS FOR DETERMINING DISEASE PROGRESSION IN NONALCOHOLIC STEATOHEPATITIS (NASH)

RELATED APPLICATIONS

This application claims priority to U.S. Provisional Patent Application Ser. No. 61/298,409, filed on Jan. 26, 2010, which is hereby incorporated by reference in its entirety.

STATEMENT REGARDING FEDERALLY SPONSORED R&D

This invention was made with government support under HD028827, DK084310, and DK080888 awarded by National Institutes of Health. The government has certain rights in the invention.

REFERENCE TO SEQUENCE LISTING

The present application is filed with a Sequence Listing in Electronic format. The Sequence Listing is provided as a file entitled "2014-02-03 Sequence list—CHMC38.001A.txt", created Feb. 3, 2014, which is approximately 4 kb in size. The information in the electronic format of the sequence listing is incorporated herein by reference in its entirety.

BACKGROUND OF THE INVENTION

Epidemiologic data suggest that there has been a significant rise in calories from saturated fat and fructose rich foods in the western world (Bray G A et al., Consumption of high-fructose corn syrup in beverages may play a role in the epidemic of obesity. *Am J Clin Nutr* 2004; 79:537-543). This increase in consumption has been paralleled by an increasing prevalence of obesity and its associated hepatic comorbidity, nonalcoholic fatty liver disease (NAFLD) (Cave M et al., Nonalcoholic fatty liver disease: predisposing factors and the role of nutrition. *J Nutr Biochem* 2007; 18:184-195). Studies of NAFLD indicate that the presence of fibrosis within the more severe phenotype, nonalcoholic steatohepatitis (NASH), is an important predictor of adverse long-term health outcomes.

Understanding the progression of fibrosis in NASH has been hampered by the lack of a comprehensive and physiologic small animal model of NASH with fibrosis. To date, small animal models of NASH with fibrosis involve either genetic manipulation (Watanabe S et al., Hepatocyte-specific Pten-deficient mice as a novel model for nonalcoholic steatohepatitis and hepatocellular carcinoma. *Hepatol Res* 2005; 33:161-166; Saxena N K et al., Leptin in hepatic fibrosis: evidence for increased collagen production in stellate cells and lean littermates of ob/ob mice. *Hepatology* 2002; 35: 762-771; Oben J A, et al., Norepinephrine induces hepatic fibrogenesis in leptin deficient ob/ob mice. *Biochem Biophys Res Commun* 2003; 308:284-292), forced overfeeding (Baumgardner J N et al., A new model for nonalcoholic steatohepatitis in the rat utilizing total enteral nutrition to overfeed a high-polyunsaturated fat diet. *Am J Physiol Gastrointest Liver Physiol* 2008; 294:G27-38), or contrived diets deficient in methionine and choline (MCD) (Leclercq I A et al., CYP2E1 and CYP4A as microsomal catalysts of lipid peroxides in murine nonalcoholic steatohepatitis. *J Clin Invest* 2000; 105:1067-1075; George J et al., Lipid peroxidation, stellate cell activation and hepatic fibrogenesis in a rat model of chronic steatohepatitis. *J Hepatol* 2003; 39:756-764; Sahai A et al., Upregulation of osteopontin expression is involved in the development of nonalcoholic steatohepatitis in a dietary murine model. *Am J Physiol Gastrointest Liver Physiol* 2004; 287:G264-273; Rinella M E et al., Mechanisms of hepatic steatosis in mice fed a lipogenic methionine choline-deficient diet. *J Lipid Res* 2008; 49:1068-1076). These models fail to map to key aspects of what occurs in human beings. For example, few humans experience diets that are deficient in methionine and choline. Moreover, rodents exposed to MCD diets are not obese. Rather, they lose weight and actually become more insulin sensitive (Rinella M E et al., Mechanisms of hepatic steatosis in mice fed a lipogenic methionine choline-deficient diet. *J Lipid Res* 2008; 49:1068-1076).

SUMMARY OF THE INVENTION

The present invention pertains to biomarkers, methods, and animal models related to fatty liver disease (FLD), including nonalcoholic steatohepatitis (NASH).

In some embodiments, methods of determining the presence of fatty liver disease (FLD) in a patient are provided, comprising: providing a sample from a patient; measuring the level of coenzyme Q (CoQ) in the sample; and comparing the CoQ value from the patient with a threshold value, wherein if the CoQ value meets the threshold value the patient is determined to be at risk for fatty liver disease. In certain embodiments, the CoQ measurement is a measurement of reduced CoQ. In certain embodiments, the CoQ measurement is a measurement of total CoQ. In certain embodiments, the CoQ measurement is a measurement of oxidized CoQ. In certain embodiments, the CoQ measurement is a measurement of coenzyme Q10 (CoQ10). In certain embodiments, the CoQ measurement is the ratio of reduced CoQ10:total CoQ10. In certain embodiments, the sample is selected from the group consisting of blood, plasma, serum, or a tissue. In certain embodiments, the sample is plasma. In certain embodiments, the threshold value is determined using a value calculated using a receiver operating characteristic (ROC) analysis. In certain embodiments, the method further comprises adjusting the measurement of reduced CoQ based on a lipid level in the sample to form an adjusted CoQ value. In certain embodiments, the measurement of reduced CoQ is adjusted for the total cholesterol level in the sample. In certain embodiments, the threshold value is a median reduced CoQ of less than about 0.17 µmol CoQ10/mmol lipid. In certain embodiments, the measurement of reduced CoQ is adjusted for the low-density lipoprotein (LDL) level in the sample. In certain embodiments, the threshold value is a median reduced CoQ of less than about 0.293 µmol CoQ10/mmol lipid. In certain embodiments, the measurement of reduced CoQ is adjusted for the triglyceride level in the sample. In certain embodiments, the threshold value is a median reduced CoQ of less than about 0.63 µmol CoQ10/mmol lipid. In certain embodiments, the measurement of reduced CoQ is adjusted for the total cholesterol level and the triglyceride level in the sample. In certain embodiments, the threshold value is a median reduced CoQ of less than about 0.131 µmol CoQ10/mmol lipid. In certain embodiments, the measurement of reduced CoQ is adjusted for the high-density lipoprotein (HDL) level in the sample. In certain embodiments, the threshold value is a median reduced CoQ of more than about 0.639 µmol of CoQ10/mmol lipid. In certain embodiments, the method further comprises adjusting the measurement of total CoQ based on a lipid level in the sample to form an adjusted CoQ value. In certain embodiments, the measurement of total CoQ is adjusted for the total cholesterol level in the sample. In certain embodiments, the threshold value is a median total CoQ of less than about 0.176 μmol CoQ10/mmol lipid. In certain embodiments, the measurement of total CoQ is adjusted for the low-density lipoprotein (LDL) level in the sample. In certain embodiments, the threshold value is a median total CoQ of less than about 0.307 μmol CoQ10/mmol lipid. In certain embodiments, the measurement of total CoQ is adjusted for the triglyceride level in the sample. In certain embodiments, the threshold value is a median total CoQ of less than about 0.92 μmol CoQ10/mmol lipid. In certain embodiments, the measurement of total CoQ is adjusted for the total cholesterol level and the triglyceride level in the sample. In certain embodiments, the threshold value is a median total CoQ of less than about 0.142 μmol CoQ10/mmol lipid. In certain embodiments, the measurement of total CoQ is adjusted for the high-density lipoprotein (HDL) level in the sample. In certain embodiments, the threshold value is a median total CoQ of more than about 0.678 μmol CoQ10/mmol lipid. In certain embodiments, the method further comprises adjusting the measurement of oxidized CoQ based on a lipid level in the sample to form an adjusted CoQ value. In certain embodiments, the measurement of oxidized CoQ is adjusted for the total cholesterol level in the sample. In certain embodiments, the threshold value is a median oxidized CoQ of less than about 0.016 μmol CoQ10/mmol lipid. In certain embodiments, the measurement of oxidized CoQ is adjusted for the low-density lipoprotein (LDL) level in the sample. In certain embodiments, the threshold value is a median oxidized CoQ of less than about 0.015 μmol CoQ10/mmol lipid. In certain embodiments, the measurement of oxidized CoQ is adjusted for the triglyceride level in the sample. In certain embodiments, the threshold value is a median oxidized CoQ of less than about 0.051 μmol CoQ10/mmol lipid. In certain embodiments, the measurement of oxidized CoQ is adjusted for the total cholesterol level and the triglyceride level in the sample. In certain embodiments, the threshold value is a median oxidized CoQ of less than about 0.006 μmol CoQ10/mmol lipid. In certain embodiments, the measurement of oxidized CoQ is adjusted for the high-density lipoprotein (HDL) level in the sample. In certain embodiments, the threshold value is a median oxidized CoQ of more than about 0.051 μmol of oxidized CoQ10/mmol lipid. In certain embodiments, the ratio of reduced CoQ10:total CoQ10 is less than about 0.935. In certain embodiments, the method further comprises determining the stage of FLD in the patient. In certain embodiments, the stage of FLD is nonalcoholic fatty liver disease (NAFLD). In certain embodiments, the stage of FLD is nonalcoholic steatohepatitis (NASH). In certain embodiments, the method further comprises determining the stage of fibrosis in NASH in the patient.

DETAILED DESCRIPTION OF THE PREFERRED EMBODIMENT

Figure 1A:
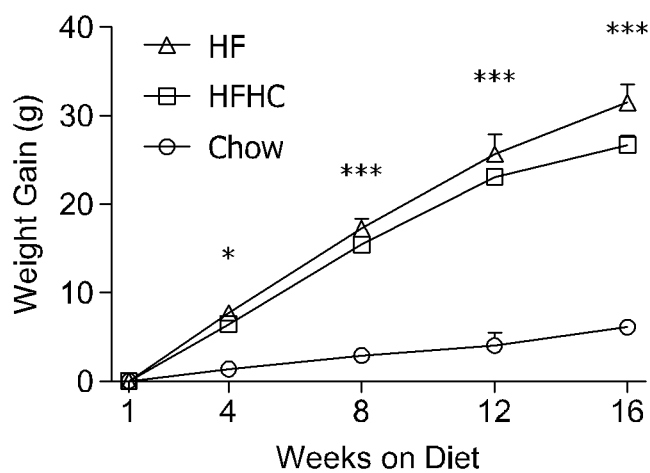
FIG. 1 shows a comparison of weight gain, body fat mass, glucose level, insulin level, and insulin resistance (FIGS. 1A-1E, respectively) in mice fed a chow diet, a high-fat, a high fat diet (HF) diet, or a high-carbohydrate (HFHC) diet.

Described herein are biomarkers, methods, and animal models related to fatty liver disease (FLD), including nonalcoholic steatohepatitis (NASH). The data provided herein demonstrates that non-genetically modified mice maintained on a HFHC diet develop obesity, demonstrate increased hepatic oxidative stress, and produce a NASH-like phenotype with significant fibrosis. In addition, the data provided herein demonstrates that particular forms of CoQ can be used to identify advancing fibrosis and fulfill the role of highly discriminatory non-invasive plasma biomarkers for fibrosis in NASH.

Some embodiments provide the novel use of an ad libitum dietary model for NASH with fibrosis and obesity using a non-genetically modified mouse. In some embodiments, it was discovered that mice exposed to a diet similar to that eaten in the western world develop a NASH phenotype associated with increased hepatic oxidative stress. In some embodiments, these mice were found to exhibit increased plasma levels of the respiratory-chain component, oxidized coenzyme Q9 ($_{ox}$CoQ9). Some embodiments provide a mechanistic link between elevated CoQ levels and increased hepatic fibrosis.

In some embodiments, a biomarker for the prediction of NASH is provided. For example, in some embodiments, the biomarker indicates an increased risk for developing NASH.

In some embodiments, the biomarker indicates earlier onset for developing NASH. In some embodiments, the biomarker indicates accelerated progression of NASH. In some embodiments, the biomarker indicates greater severity of NASH. In some embodiments, the biomarker indicates greater risk of morbidity for an individual with NASH.

In some embodiments, a biomarker is synthesized in hepatocytes. In a preferred embodiment, a biomarker is synthesized in mitochondria. In some embodiments, a biomarker exhibits antioxidant properties.

Given that hepatic reactive oxygen species (ROS) is a chronic insult in human NASH, the HFHC fed mice described herein can be observed for ROS levels. In some embodiments, ROS levels are compared to those in HF fed mice. For example, ROS levels can be compared in HFHC fed mice and HF diet mice. In some embodiments, ROS levels are compared to those in HC fed mice. In some embodiments, ROS levels are compared to those in chow fed mice. For example, ROS levels can be compared in HFHC fed mice and chow fed mice. In some embodiments, the ROS levels are cytoplasmic ROS levels.

In some embodiments, a sample is collected from a patient and the level of reduced coenzyme Q ($_{red}$CoQ) is determined. In some embodiments, the sample is a bodily fluid. In some embodiments, the bodily fluid is blood, plasma, serum, or a tissue. In a preferred embodiment, the bodily fluid is plasma. In preferred embodiments, the biomarkers described herein are readily accessible by peripheral blood draw.

In some embodiments, levels of $_{red}$CoQ in a mammal having NASH without fibrosis are determined to be higher than the $_{red}$CoQ levels of a control mammal without NASH. In some embodiments, levels of $_{red}$CoQ in a mammal having NASH with fibrosis are determined to be higher than the $_{red}$CoQ levels of levels of a mammal having NASH without fibrosis.

In some embodiments, a $_{red}$CoQ level serves a biomarker for FLD or NASH. In some embodiments, a $_{red}$CoQ level serves a biomarker for establishing disease severity at diagnosis. In some embodiments, a $_{red}$CoQ level serves as a biomarker to monitor disease progression. In some embodiments, a $_{red}$CoQ level serves as a biomarker to evaluate response to treatment.

In some embodiments, a sample is collected from a patient and the level of oxidized coenzyme Q ($_{ox}$CoQ) is determined. In some embodiments, the sample is a bodily fluid. In some embodiments, the bodily fluid is blood, plasma, serum, or a tissue. In a preferred embodiment, the bodily fluid is plasma.

In some embodiments, levels of $_{ox}$CoQ in a mammal having NASH without fibrosis are determined to be higher than the $_{ox}$CoQ levels of a control mammal without NASH. In some embodiments, levels of $_{ox}$CoQ in a mammal having NASH with fibrosis are determined to be higher than the $_{ox}$CoQ levels of levels of a mammal having NASH without fibrosis. For example, in some embodiments, $_{ox}$CoQ levels are shown to be elevated in mice with advanced fibrosis in the non-genetically altered dietary model of NASH that is described herein. In some embodiments, $_{ox}$CoQ levels are shown to be elevated in obese humans.

In some embodiments, an $_{ox}$CoQ level serves a biomarker for FLD or NASH. In some embodiments, an $_{ox}$CoQ level serves a biomarker for establishing disease severity at diagnosis. In some embodiments, an $_{ox}$CoQ level serves as a biomarker to monitor disease progression. In some embodiments, an $_{ox}$CoQ level serves as a biomarker to evaluate response to treatment.

In some embodiments, a sample is collected from a patient and the level of total coenzyme Q (total CoQ) is determined. In some embodiments, the sample is a bodily fluid. In some embodiments, the bodily fluid is blood, plasma, serum, or a tissue. In a preferred embodiment, the bodily fluid is plasma.

In some embodiments, levels of total CoQ in a mammal having NASH without fibrosis are determined to be higher than the total CoQ levels of a control mammal without NASH. In some embodiments, levels of total CoQ in a mammal having NASH with fibrosis are determined to be higher than the total CoQ levels of levels of a mammal having NASH without fibrosis.

In some embodiments, a total CoQ level serves a biomarker for FLD or NASH. In some embodiments, a total CoQ level serves a biomarker for establishing disease severity at diagnosis. In some embodiments, a total CoQ level serves as a biomarker to monitor disease progression. In some embodiments, a total CoQ level serves as a biomarker to evaluate response to treatment.

In some embodiments, the biomarker is a mammalian biomarker. In some embodiments, the biomarker is a human biomarker. In some embodiments, the biomarker is a rodent biomarker. In some embodiments, the level of CoQ10 (the predominant form of CoQ in humans) serves as a biomarker. In some embodiments, the level of CoQ9 (the predominant form of CoQ in rodents) serves as a biomarker.

In some embodiments, levels of the oxidized form of $_{ox}$CoQ9 are investigated. In some embodiments, plasma levels of $_{ox}$CoQ9 correlate with collagen 1 mRNA in liver tissue. In some embodiments, plasma levels of $_{ox}$CoQ9 discriminate between NASH with fibrosis and NASH without fibrosis. For example, in some embodiments, HFHC (NASH with fibrosis) mice demonstrate higher levels of $_{ox}$CoQ9 than HF (NASH without fibrosis) or chow (normal histology) mice. In some embodiments, $_{ox}$CoQ is used as a biomarker for fibrosis in NASH. In some embodiments, plasma $_{ox}$CoQ9 is used as a biomarker for NASH.

In some embodiments, obese patients with NAFLD or NASH demonstrate alterations in levels of coenzyme Q. In some embodiments, levels of total CoQ, CoQ$_{ox}$ or CoQ$_{red}$ discriminate fibrotic NASH from non-fibrotic FLD and normal liver histology. In some embodiments, levels of total CoQ, CoQ$_{ox}$ or CoQ$_{red}$ discriminate non-fibrotic FLD from normal liver histology. In some embodiments, imbalances in CoQ redox status are evaluated to identify NAFLD or NASH. For example, in some embodiments, serum CoQ is found to be significantly higher in patients with fibrotic NASH than patients with NAFLD without fibrosis and normal patients.

In some embodiments, the biomarkers provided herein are used to discriminate between fibrotic NASH and steatosis. In some embodiments, a biomarker provided herein is used to discriminate between fibrotic NASH and steatosis+inflammation. In some embodiments, a biomarker provided herein is used to discriminate between fibrotic NASH and a normal condition.

In some embodiments, the biomarkers described herein are used in combination with other putative biomarkers for NASH. For example, in some embodiments, a biomarker described herein is assessed in conjunction with soluble cytokeratin 18 fragments [32].

In some embodiments, ROC analysis is used to calculate thresholds for reduced, oxidized, or total CoQ. In preferred embodiments, ROC parameters are adjusted for lipoproteins, such as TC, LDL, HDL, TG, and TG+TC.

In some embodiments, reduced CoQ10 adjusted for LDL is less than about 0.293 μmol CoQ10/mmol lipid. In some embodiments, reduced CoQ10 adjusted for TC is less than about 0.170 μmol CoQ10/mmol lipid. In some embodiments, reduced CoQ10 adjusted for TG is less than about 0.63 μmol CoQ10/mmol lipid. In some embodiments, reduced CoQ10 adjusted for TC+TG is less than about 0.131 µmol CoQ10/mmol lipid. In some embodiments, reduced CoQ10 adjusted for HDL is more than about 0.639 µmol CoQ10/mmol lipid.

In some embodiments, total CoQ10 adjusted for LDL is less than about 0.3068 µCoQ10/mmol lipid. In some embodiments, total CoQ10 adjusted for TC is less than about 0.1757 µmol CoQ10/mmol lipid. In some embodiments, total CoQ10 adjusted for HDL is more than about 0.678 µmol CoQ10/mmol lipid. In some embodiments, total CoQ10 adjusted for TG is less than about 0.9199 µmol CoQ10/mmol lipid. In some embodiments, total CoQ10 adjusted for TC+TG is less than about 0.142 µmol CoQ10/mmol lipid.

In some embodiments, oxidized CoQ10 adjusted for LDL is less than about 0.0152 µmol CoQ10/mmol lipid. In some embodiments, oxidized CoQ10 adjusted for TC is more than about 0.016 µmol CoQ10/mmol lipid. In some embodiments, oxidized CoQ10 adjusted for HDL is more than about 0.051 µmol CoQ10/mmol lipid. In some embodiments, oxidized CoQ10 adjusted for TG is less than about 0.0505 µmol CoQ10/mmol lipid. In some embodiments, oxidized CoQ10 adjusted for TC+TG is less than about 0.006 µmol CoQ10/mmol lipid.

In some embodiments, patients identified as having NAFLD or NASH have a BMI greater than about 25 mg/kg$^2$. In some embodiments, patients identified as having NAFLD or NASH have a BMI greater than about 30 mg/kg$^2$. In some embodiments, patients identified as having NAFLD or NASH have a BMI greater than about 35 mg/kg$^2$. In some embodiments, patients identified as having NAFLD or NASH have a BMI greater than about 40 mg/kg$^2$. In some embodiments, patients identified as having NAFLD or NASH are overweight. In some embodiments, patients identified as having NAFLD or NASH are obese. In some embodiments, patients identified as having NAFLD or NASH are morbidly obese.

In some embodiments, the high-fat diet for the mouse model described herein provides between 48% and 52% of calories from fat. For example, the high-fat diet can provide about 48%, 49%, 50%, 51%, and 52% of calories from fat. In a preferred embodiment, the high-fat-diet provides 58% of calories from fat (comprising mainly medium chain saturated fat), and fructose and sucrose in regular drinking water. In some embodiments, the high-fat diet results in mice developing fibrosis. In some embodiments, the high-fat diet results in mice developing stage 2 fibrosis.

In some embodiments, the high-carbohydrate diet for the mouse model described herein provides between 45% w/v and 55% w/v of fructose. For example, the high-fat diet can provide about 45%, 46%, 47%, 48%, 49%, 50%, 51%, 52%, 53%, 54%, and 55% fructose w/v. In a preferred embodiment, the high-carbohydrate diet provides 55% fructose w/v.

In some embodiments, mice are provided ad-libitum access to a high calorie diet consisting predominantly of medium chain saturated fat and fructose. In some embodiments, the high calorie diet increases hepatic ROS and generates significant fibrosis. In preferred embodiments, ad libitum access to the high calorie diet yields obesity, insulin resistance, and NASH with fibrosis in a non-genetically modified mouse within 16 weeks. In some embodiments, this phenotype can develop in the background of increased hepatic ROS, pro-inflammatory macrophages, TGF-β, and collagen 1 mRNA.

In some embodiments, HF-fed mice are compared to mice maintained on the same diet, but also given ad libitum access to fructose in their drinking water (HFHC). In some embodiments, mice fed a HFHC diet are monitored for increased hepatic oxidative stress. In some embodiments, mice fed a HFHC diet are monitored for CD11b+F4/80+Gr1+ macrophages in the liver. In some embodiments, mice fed a HFHC diet are monitored for TGF-β1 driven fibrogenesis and collagen deposition compared to weight-matched controls in a HF fed group. In some embodiments, fructose consumption is modified to observe the progression of liver fat deposition to fibrogenesis. In some embodiments, intrahepatic CD11+F4/80+Gr1+ monocyte-derived macrophages are 10-fold higher than either chow or HF diet fed mice, with 50% of the macrophages in HFHC livers being Gr1+.

In some embodiments, a fructose-enriched HFHC diet produces an increased ROS signature in the liver (possibly from mitochondrial injury and/or dysfunction), and results in histologically visible hepatic fibrosis. This can be associated with an increase in the number of CD11b+F4/80+Gr1+ macrophages in the liver, and an enhanced TGF-β1 and collagen 1 mRNA signature.

It will be understood by those of skill in the art that numerous and various modifications can be made without departing from the spirit of the present invention. All the references referred to herein are incorporated by reference in their entirety for the subject matter discussed. The following examples are included for illustrative purposes only and are not intended to limit the scope of the invention.

Example 1

NASH Mouse Model

Six to eight week old male C57B1/6 mice (Jackson Laboratory, Bar Harbor, Me.) were group-housed in cages in a temperature-controlled vivarium (22±2° C.) on a 12-h light, 12-h dark schedule at the University of Cincinnati. Animals were randomly assigned to either chow diet (Teklad; Harlan, Madison, Wis.); a high-fat (HF) diet (Surwit diet, 58 kcal, % fat mainly from medium chain saturated triglycerides) (Research Diets, New Brunswick, N.J.); or a high-fat high-carbohydrate (HFHC) diet (Surwit diet and drinking water enriched with high fructose corn syrup equivalent (55% fructose) (Acros Organics, Morris Plains, N.J.) and 45% sucrose (Sigma-Aldrich, St. Louis, Mo.) by weight in drinking water at a concentration of 42 g/L). Animals were provided ad libitum access to these diets for 16 weeks. Body weights were measured weekly, while percent body fat was measured at 12 weeks using Echo MRI (Echo MRI Whole Body Composition Analyzer; Echo Medical Systems, Houston, Tex.). All animal experiments were approved by the Institutional Animal Care and Use Committee of the University of Cincinnati and Cincinnati Children's Hospital Medical Center (CCHMC).

Example 2

Body Weight, Body Composition, and Insulin Resistance in NASH

Statistical comparison between groups and treatments was performed using one way ANOVA and post-hoc Tukey's test. Student's T-tests were used when comparing two groups. A p-value of <0.05 was considered statistically significant. Data was presented as mean±SEM.

Figure 1B:
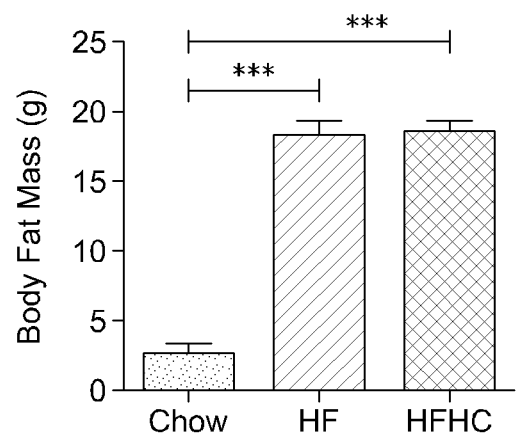

Mice fed the HFHC and HF diets as described in Example 1 gained more weight than the mice fed the chow diet. The body weight of HFHC diet fed mice were significantly greater than chow fed mice starting at 2 weeks (chow: 25.8±0.5 g vs. HFHC: 28.1±0.3 g; p=0.016). HFHC and HF diet fed mice continued to gain significantly more weight and had a mean body weight of 50.5±0.8 g and 53.18±1.8 g, respectively, compared to chow fed mice that had a mean body weight of 31.94±0.2 g at 16 weeks (FIG. 1A). Total body fat mass estimation by MR at 12 weeks demonstrated that HFHC fed mice (18.66±0.7 g) and HF-fed mice (18.40±0.9 g) had significantly greater body fat compared to chow-fed mice (2.82±0.6 g; p<0.0001) (FIG. 1B).

Figure 1C:
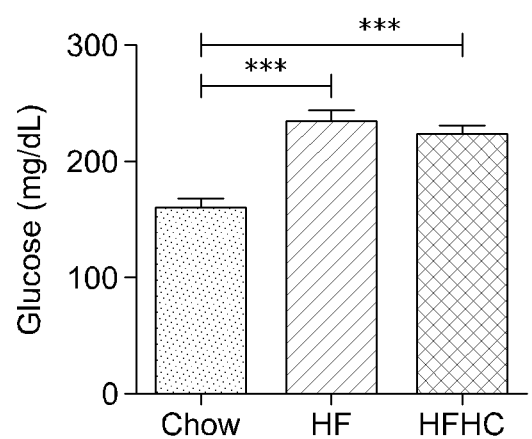
Figure 1D:
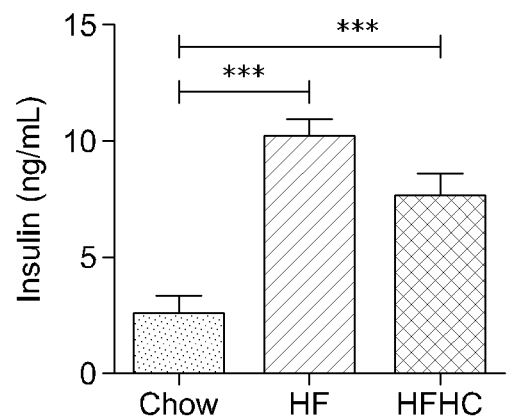
Figure 1E:
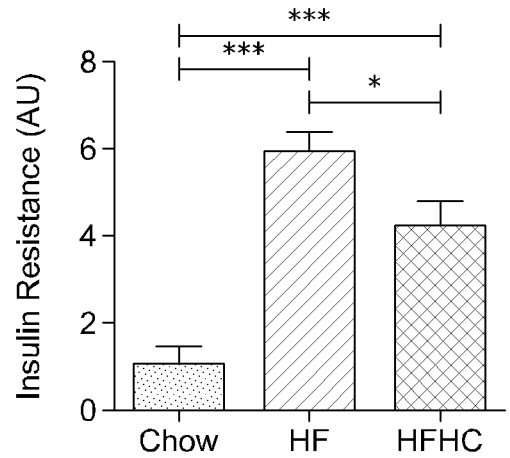

Glucose measurements were obtained via tail-vein bleeds at 12 weeks after a 4 hour fast using an ACCU-CHEK® Advantage glucose meter (ACCU-CHEK®, Roche Diagnostics, Indianapolis, Ind.). Plasma insulin content was measured using an Ultra Sensitive Mouse Insulin ELISA Kit (Crystal Chem, Downers Grove, Ill.). Insulin resistance was calculated using homeostasis model assessment insulin resistance (HOMA-IR) (Akagiri S et al., A Mouse Model of Metabolic Syndrome; Increase in Visceral Adipose Tissue Precedes the Development of Fatty Liver and Insulin Resistance in High-Fat Diet-Fed Male KK/Ta Mice. J Clin Biochem Nutr 2008; 42:150-157). Fasting plasma glucose levels were higher in HFHC (223.6±7 mg/dL) and HF (235.4±10 mg/dL) diet fed mice than chow diet fed mice (160.4±7.3 mg/dL) (p<0.0001) (FIG. 1C). Similarly, fasting insulin was also higher in HFHC fed mice (7.7±1 ng/mL) and HF diet fed mice (10.3±0.9 ng/ml) compared to chow fed mice (1.9±0.1 ng/mL) (p<0.0001) (FIG. 1D). The glucose and insulin values were used to estimate insulin resistance as HOMA-IR calculations, and both HFHC (4.2±0.6) and HF (5.9±0.5) diet fed mice were significantly insulin resistant compared to chow diet fed mice (1.1±0.4) (p<0.0001) (FIG. 1E). Thus, both HFHC and HF mice were significantly obese and insulin resistant compared to chow mice.

Example 3

Hepatic Steatosis, Inflammation, and Apoptosis in NASH

Liver sections for histology were obtained at 16 weeks for the mice generated in Example 1. Animals were euthanized in a $CO_2$ chamber and the livers were harvested. A 10% formalin fixed specimen was stained with hematoxylin & eosin (H&E) or trichrome stain by CCHMC's Department of Pathology. NAFLD activity score (NAS) was assigned by a single independent pathologist, blinded to experimental design and treatment groups. Briefly, steatosis was graded (0-3), lobular inflammation was scored (0-3), and ballooning was rated (0-2), producing a NAS score range from 0 to 8 (30). Fibrosis was staged separately on a scale (0-4). TUNEL staining was performed as previously described (Feldstein A E et al., Hepatocyte apoptosis and fas expression are prominent features of human nonalcoholic steatohepatitis. *Gastroenterology* 2003; 125:437-443).

Liver triglyceride content was determined at 16 weeks, as previously described (Sahai A et al., Insulin-resistant and diabetic db/db mice develop marked liver fibrosis in a dietary model of nonalcoholic steatohepatitis. Submitted for publication 2004). Briefly, 100 milligrams of wet liver tissue was homogenized in a buffer consisting of 50 mM Tris, 150 mM NaCl, 1 mM EDTA, and protease inhibitor. The enzymatic triglyceride assay was performed using a Triglyceride Reagent Set (Pointe Scientific, Inc., Canton, Mich.). Photometric absorbance was read at 500 nm using a Synergy 2 microplate reader (BIOTEK®, Winooski, Vt.). Blood was collected at 16 weeks and used to measure ALT with a DISCRETPAK™ ALT Reagent Kit (Catachem, Bridgeport, Conn.).

Figure 2A:
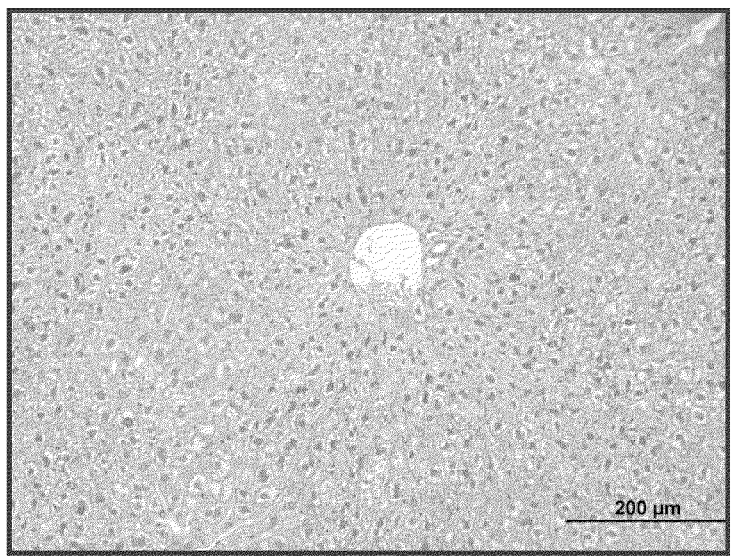
FIG. 2 shows histological sections of livers from mice fed a chow diet, a HF diet, or a HFHC diet (FIGS. 2A-2C, respectively); and a comparison of hepatic triglyceride levels, plasma alanine aminotransferase (ALT) levels, and liver weight (FIGS. 2D-2F, respectively) in mice fed a chow diet, a HF diet, or a HFHC diet.
Figure 2B:
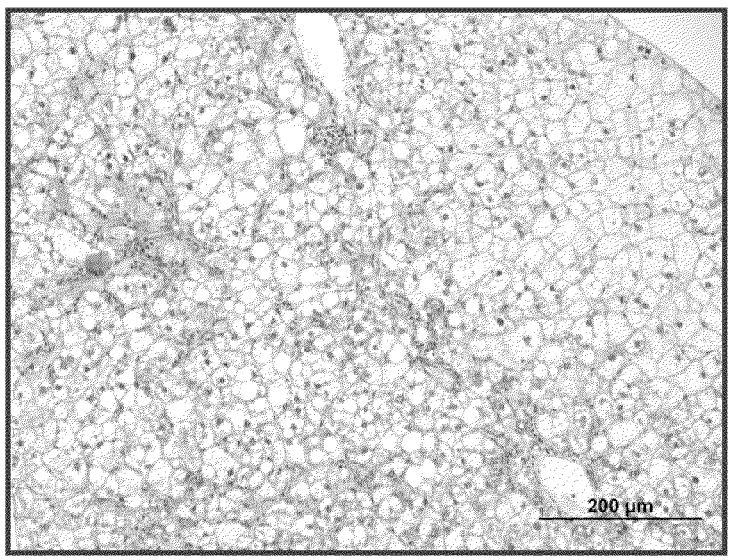
Figure 2C:
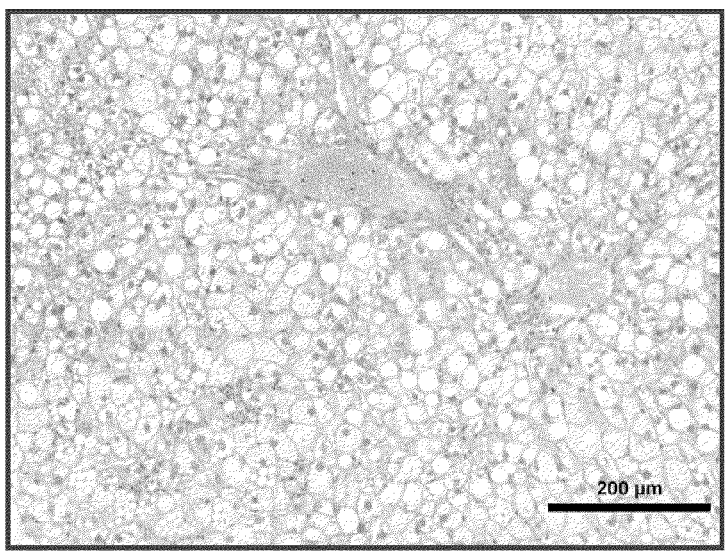

Histological examination of livers from HFHC and HF diet fed mice demonstrated substantial steatosis with inflammatory changes. Micro and macrovesicular steatosis were clearly visible on routine histology staining with H&E after 16 weeks (FIGS. 2B and 2C). There were ballooned hepatocytes (inserts in FIGS. 2B and 2C) and a predominantly lymphocytic lobular inflammation. The additional fructose and sucrose in the drinking water of HFHC diet fed mice did not result in a markedly different amount of steatosis. Inflammatory foci were scattered across the lobule and portal inflammation was also seen (inserts in FIGS. 2B and 2C).

Figure 2D:
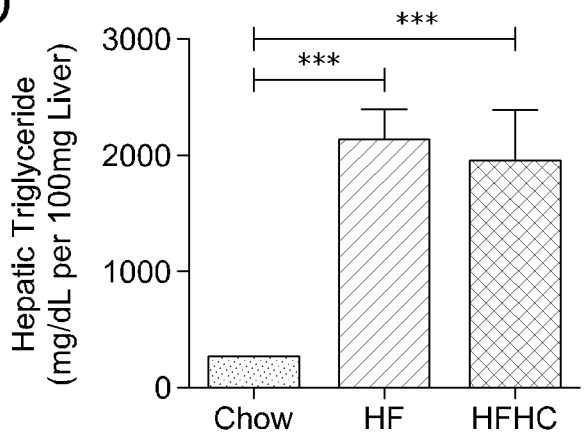

HFHC and HF diet fed mice had higher steatosis grades, ballooning scores, and NAFLD activity scores (NAS) than chow fed mice (1 way ANOVA; p<0.0001 in all three categories) (Table 1). For example, both HFHC (5.17±0.8) and HF (5.25±0.2) diet fed mice had significantly higher NAS scores than chow fed mice (0.67±0.7) (p<0.0001) (Table 1). HFHC liver histology was significantly different from both HF and chow fed mice after 16 weeks of diet for fibrosis and lobular inflammation scores (1 way ANOVA; fibrosis p<0.0001 and inflammation p=0.0195). Confirming the histological impressions, the weights of the livers of HFHC and HF mice were significantly higher compared to chow fed mice (p<0.0001) (FIG. 2F). Similarly, triglyceride (TG) content at 16 weeks was higher in HFHC (1955±430 mg/dl per 100 mg wet liver) and HF mice (1096±115 mg/dl per 100 mg wet liver) compared to chow mice (276±34 mg/dl per 100 mg wet liver) (one way ANOVA; p<0.0001) (FIG. 2D).

Figure 2E:
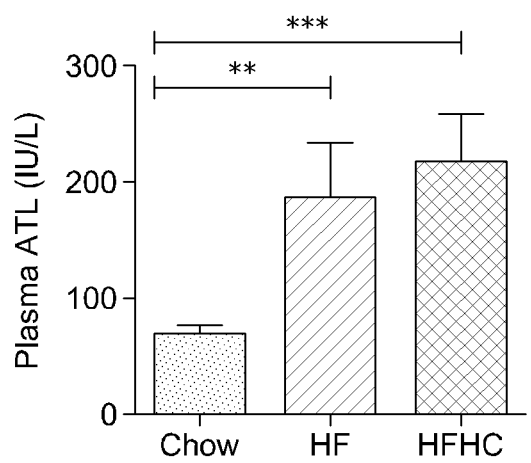
Figure 2F:
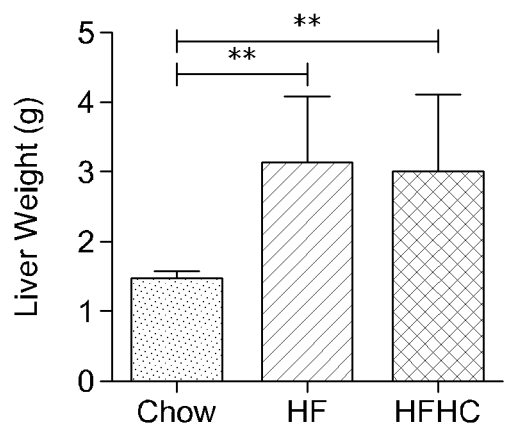

Plasma ALT levels were greater in both HFHC (217.3±40.2 IU/L) and HF mice (187±47 IU/L) at 16 weeks compared to chow fed mice (70.9±5.4 IU/L) (p<0.0001) (FIG. 2E). TUNEL staining was increased in HFHC and HF mice compared to chow mice (data not shown). Thus, both HFHC and HF mice had significantly more hepatic steatosis, inflammation, and apoptosis compared to chow mice.

TABLE 1

Histological Characteristics after 16 weeks on Diet

| Parameters | Chow | HF | HFHC |
|---|---|---|---|
| Steatosis Grade (0-3) | 0.00 ± 0.0 | 2.88 ± 0.1* | 2.50 ± 0.3* |
| Lobular Inflammation Score (0-3) | 0.42 ± 0.1 | 0.38 ± 0.3 | 1.33 ± 0.4*# |
| Ballooning Score (0-2) | 0.26 ± 0.1 | 2.00 ± 0.0*** | 1.33 ± 0.4** |
| NAS (0-8) | 0.68 ± 0.2 | 5.25 ± 0.2*** | 5.17 ± 0.8*** |
| Fibrosis Stage (0-4) | | | |
| 0(%) | 100 | 100 | 50 |
| 1(%) | 0 | 0 | 33 |
| 2(%) | 0 | 0 | 16 |
| Fibrosis Present Total (%) | 0 ± 0 | 0 ± 0 | 50 ± 22.4***## |

Tukey's post test
***= p < 0.001,
**= p < 0.01,
*= p < 0.05
*= versus chow,
versus HF
N for groups: chow = 8; HF = 8, HFHC = 6

Example 4

Hepatic Fibrosis and Pro-Fibrogenic Gene Signatures in NASH

Figure 3A:
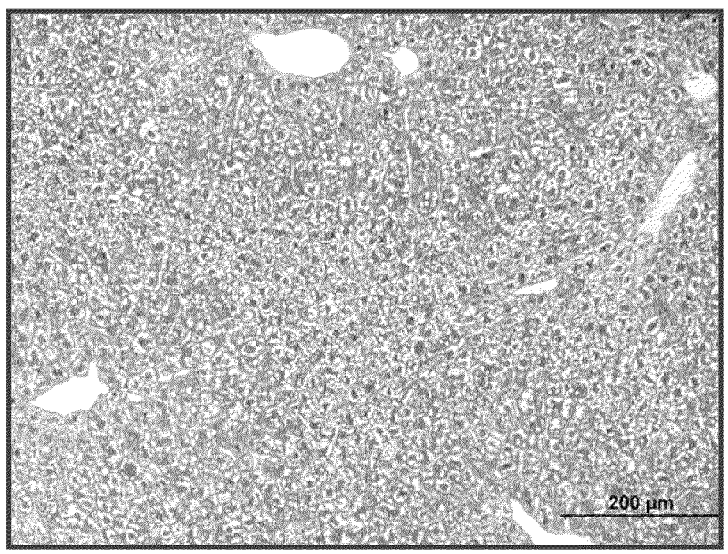
FIG. 3 shows histological sections of trichrome stained liver sections from mice fed a chow diet, a HF diet, or a HFHC diet (FIGS. 3A-3C, respectively); a comparison of hepatic Collagen 1 levels in mice fed a chow diet, a HF diet, or a HFHC diet (FIG. 3D); and a comparison of transforming growth factor β1 (TGF-β1) mRNA levels in mice fed a chow diet, a HF diet, or a HFHC diet (FIG. 3E).
Figure 3B:
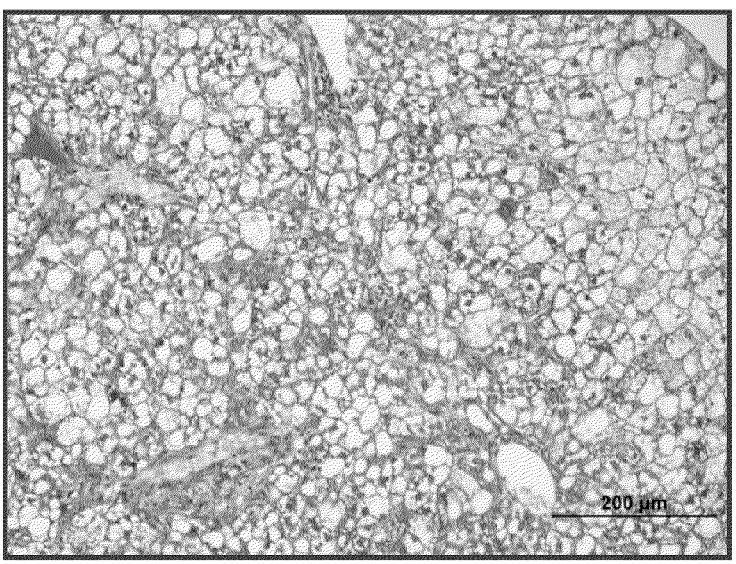
Figure 3C:
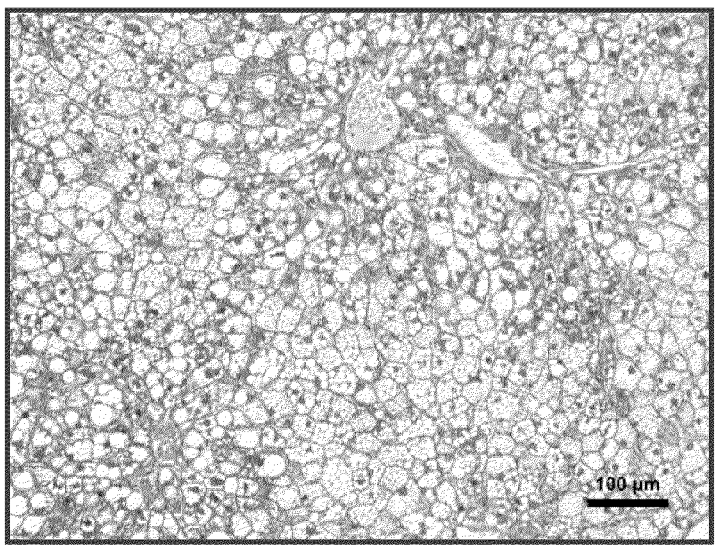

Histological examination of trichrome stained liver sections from HFHC fed mice obtained as described in Example 3 demonstrated significant fibrosis in half of the mice at 16 weeks, and 33% of mice had Stage 1a or 1c fibrosis with perisinusoidal or portal-peri-portal fibrosis, while 16% had Stage 2 fibrosis with perisinusoidal and portal-periportal fibrosis (Table 1). HF and chow diet fed mice had no evidence of significant fibrosis on histology. Perisinusoidal fibrosis in HFHC mice livers was even more pronounced in focal areas (insert in FIG. 3C).

RNA was isolated from frozen liver tissues collected and flash-frozen in 2-methylbutane (Sigma-Aldrich, St. Louis, Mo.) on dry ice and stored at −80° C. until further use. The tissue was subsequently homogenized in a buffer consisting of 50 mM Tris, 150 mM NaCl, 1 mM EDTA, and protease inhibitor. Total RNA was isolated using TRIZOL® reagent protocol (Molecular Research Center, Cincinnati, Ohio). Isolated RNA was treated with RNase-Free DNase (Fisher Scientific, Pittsburgh, Pa.), and purified on a RNeasy Mini Spin Column (Qiagen, Valencia, Calif.) before proceeding with reverse transcription. cDNA was made using TAQMAN® Reverse Transcription protocol and Eppendorf Mastercycler PCR machine (Eppendorf North America, Westbury, N.Y.). A pre-designed, validated gene-specific TAQMAN® probe was used for Collagen 1. Primer sequences for TGF-β1 were as follows: reverse CGT AGT AGA CGA TGG GCA GTG G (SEQ ID NO: 1), and forward TAT TTG GAG CCT GGA CAC ACA G (SEQ ID NO: 2). Messenger RNA expression was obtained using Stratagene SYBR® green real-time kinetic PCR on a Stratagene Mx-3005 Multiplex Quantitative PCR machine (Stratagene, Agilent Technologies, La Jolla, Calif.). Relative expression was determined by comparison of dT values relative to GAPDH expression using the 2-DDCT method.

Figure 3D:
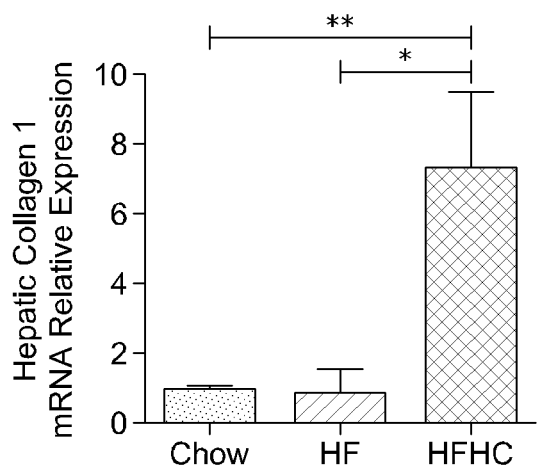
Figure 3E:
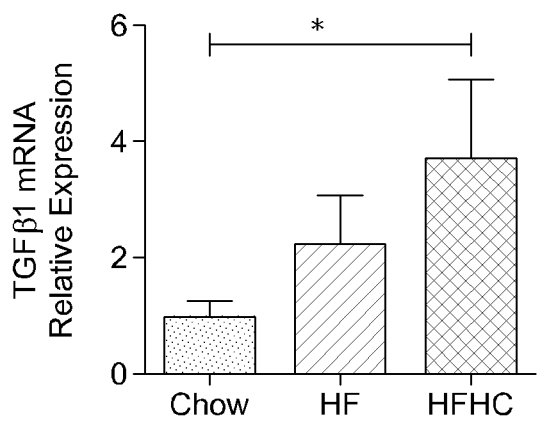

RT-PCR for Collagen 1 mRNA expression in the livers was significantly higher in HFHC diet mice (7.36±2.1 fold) compared to both HF (0.92±0.6 fold) and chow diet fed mice (1.0±0.1) at 16 weeks (p=0.0031) (FIG. 3D). Similarly, mRNA expression of TGF-β1 was significantly higher in HFHC diet fed mice (3.72±1.3 fold) and chow diet fed mice (1.0±0.2) at 16 weeks (p=0.04) (FIG. 3E). Thus, HFHC mice had significantly more hepatic fibrosis and pro-fibrogenic gene signatures compared to chow and HF mice.

Example 5

Hepatic Macrophages in NASH

Single liver cell suspensions were prepared by mincing and passing over 40 μm sterile cell strainers (Fisher Scientific, Pittsburgh, Pa.). After centrifugation at 2000 rpm, cell pellet was mixed with 33% percoll (Sigma-Aldrich, St. Louis, Mo.) in RPMI1640 solution (Invitrogen, Carlsbad, Calif.). Cell suspension was centrifuged at 2000 rpm for 20 min at room temperature (RT) without applying brakes and cell pellet was removed, washed and red blood cells were lysed with 1× lysis buffer (eBioscience, San Diego, Calif.). Cells were suspended in 500 FACS buffer (PBS containing 4% FCS and 0.1% azide) and Fc receptor was blocked with anti-mouse CD16/32 (Clone 93, eBioscience, San Diego, Calif.). Cells were stained with CD11b-PerCP-Cy5.5 (Clone M1/70), F4/80-PE (Clone BM8), and Gr1-FITC (Clone 1A8) (eBioscience, San Diego, Calif.). CD11b+ F4/80+ cells were defined as macrophages, while their pro-fibrinogenic subset was defined as CD11b+Gr1+ cells. Cells were acquired on a FACSCANTO™ Flow Cytometer (BD Biosciences, San Jose, Calif.) and data was analyzed by FlowJo software version 7.5 (TreeStar, Ashland, Oreg.).

Figure 4A:
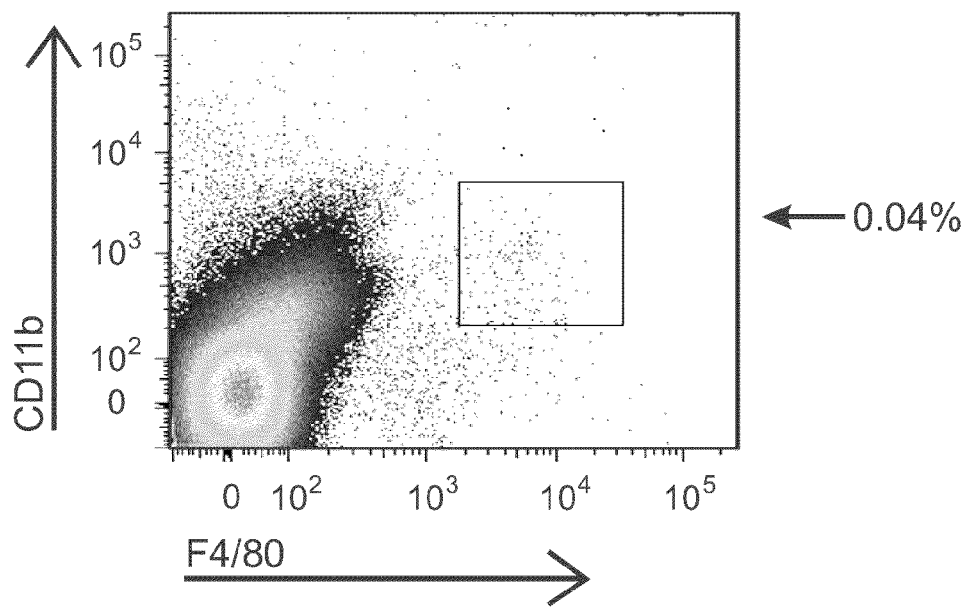
FIG. 4 shows populations of CD11b+ F4/80+ macrophage cells in liver tissue in mice fed a chow diet, a HF diet, or a HFHC diet (FIGS. 4A-4C, respectively); the mean percentage of CD11b+ F4/80+ cells in liver cells from mice fed a chow diet, a HF diet, or a HFHC diet (FIG. 4D); and the mean percentage of GR1+ macrophages in liver cells from mice fed a chow diet, a HF diet, or a HFHC diet at 16 weeks (FIG. 4E).
Figure 4B:
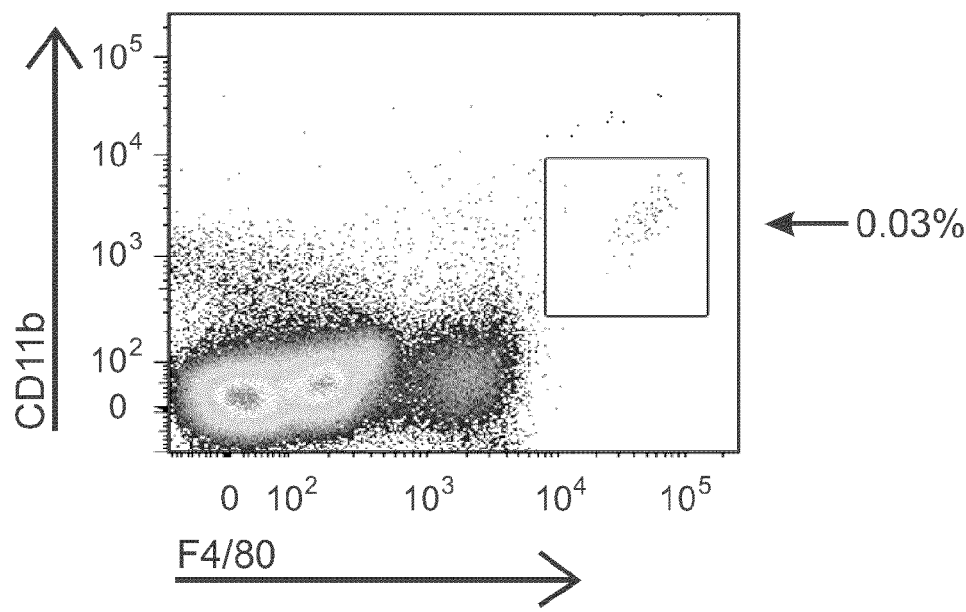
Figure 4C:
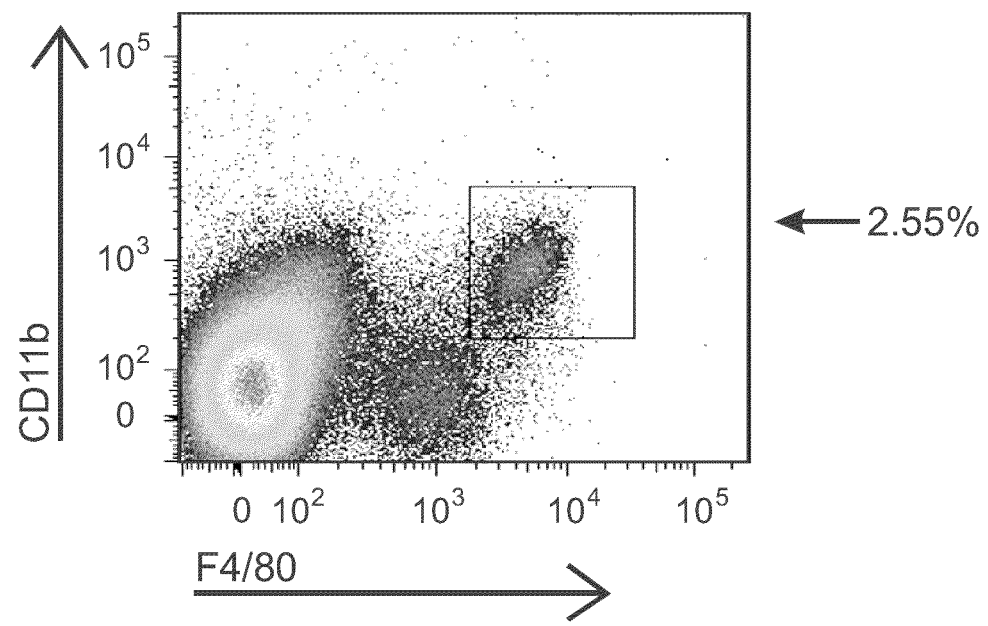
Figure 4D:
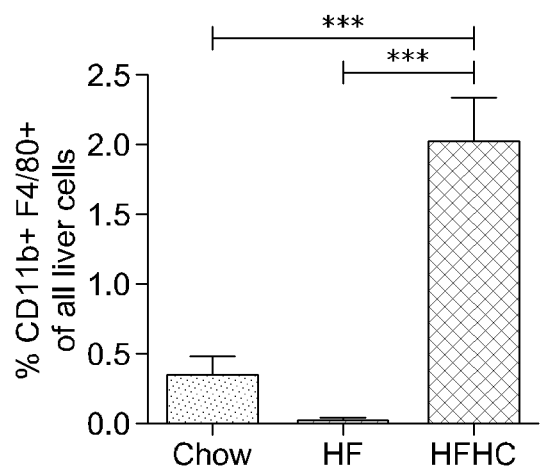
Figure 4E:
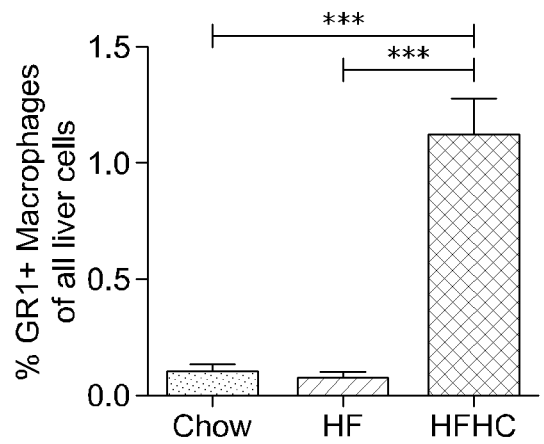

The macrophage inflammatory Gr1+ subset is massively recruited into the liver upon toxic injury (Karlmark K R et al., Hepatic recruitment of the inflammatory Gr1+ monocyte subset upon liver injury promotes hepatic fibrosis. *Hepatology* 2009; 50:261-274). FIGS. 4A-4C show examples of the selection and quantification of macrophage populations from individual mice fed a chow diet, a HF diet, or a HFHC diet, respectively. The HFHC diet fed mice had an approximately ten fold increase in the macrophage population (CD11b+F4/80+) in the liver tissue (a mean value of 2.03±0.3% of all liver cells) compared to HF diet fed mice (a mean value of 0.03±0.0%) and chow fed (a mean value of 0.35±0.1%) liver tissue (p<0.0001) (FIG. 4D). Upon gating on CD11b+F4/80+ cells, the Gr1+ subset of cells were then identified and quantified. The HFHC diet fed mice (1.12±0.2% of all liver cells) had a ten fold higher number of Gr1+ macrophages in their livers at 16 weeks compared to either HF diet fed mice (0.08±0.0% of all liver cells) or chow fed mice (0.1±0.0%) (p<0.0001) (FIG. 4E). These Gr1+ cells made up approximately 50% of the CD11bF4/80+ macrophages. The HFHC mice therefore had a significantly more pro-inflammatory macrophage population than chow and HF mice.

Example 6

Hepatic ROS and Plasma CoQ

Frozen liver sections were rehydrated in Phosphate Buffer Solution (PBS), (CELLGRO®, CellGenix, Antioch, Ill.). Stock dihydroethidium (DHE) (Sigma-Aldrich, St. Louis, Mo.) solution was diluted in dimethyl sulfoxide (DMSO) (Sigma-Aldrich, St. Louis, Mo.) to a final concentration of 10 μg/ml. Slides were incubated in DHE solution and washed with 1×PBS and coversliped using 80% glycerol in PBS. Fluorescence was recorded and quantified using Texas red filter on an upright Olympus BX51 microscope and DPControler software (Olympus; Hamburg, Germany) and IMAGE J software (NIH, Bethesda, Md.) (Wainwright M S et al., Carnitine treatment inhibits increases in cerebral carnitine esters and glutamate detected by mass spectrometry after hypoxia-ischemia in newborn rats. Stroke 2006; 37:524-530).

Figure 5A:
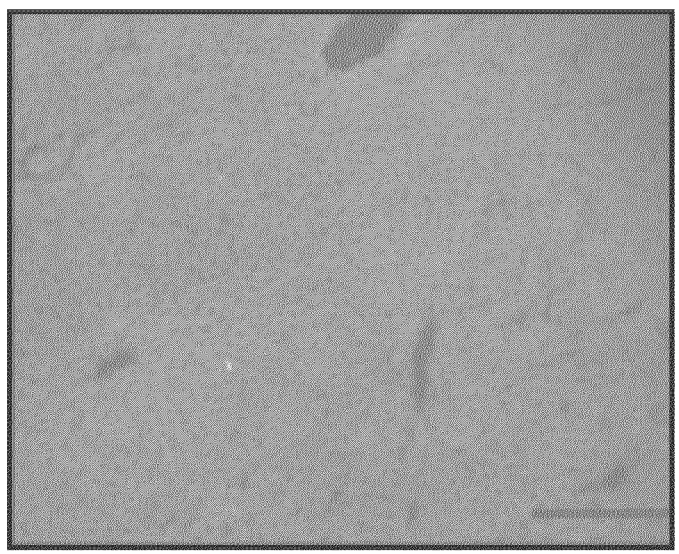
FIG. 5 shows dihydroethidium (DHE) staining for superoxide detection in frozen liver sections from mice fed a chow diet, a HF diet, or a HFHC diet (FIGS. 5A-C, respectively); average fluorescence units per high power field (FU/HPF) for DHE fluorescence in mice fed a chow diet, a HF diet, or a HFHC diet (FIG. 5D); and plasma coenzyme Q9 levels in mice fed a chow diet, a HF diet, or a HFHC diet (FIG. 5E).
Figure 5B:
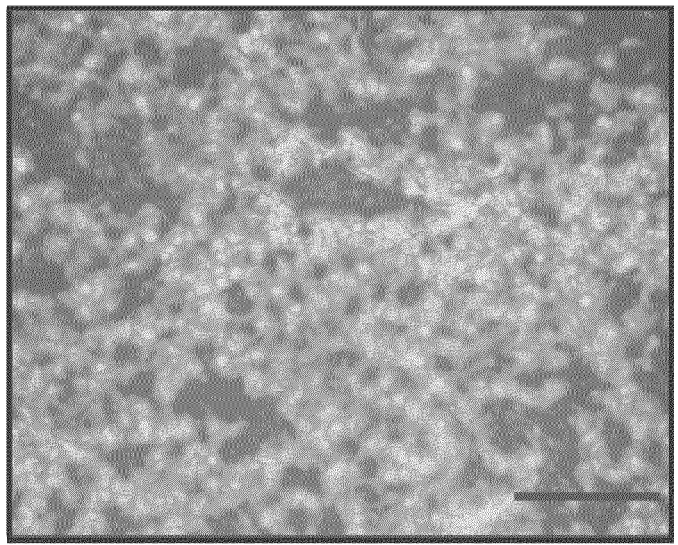
Figure 5C:
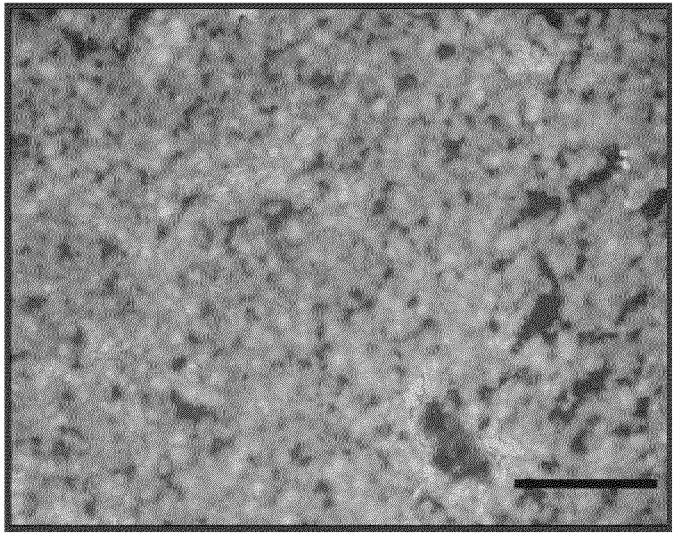
Figure 5D:
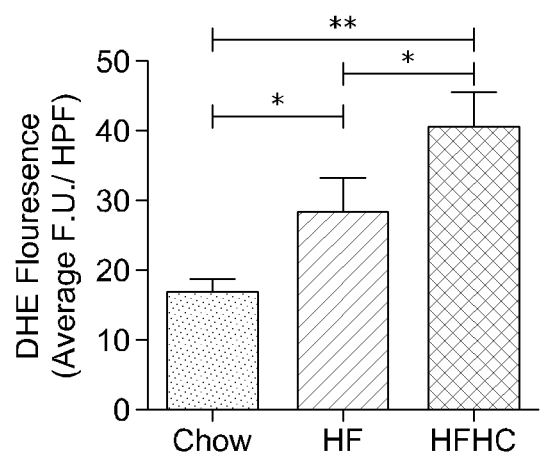

DHE staining for superoxide detection was performed on frozen liver sections and average fluorescence units per high power field (FU/HPF) were quantified using morphometric software. At 16 weeks, livers from HFHC diet fed mice had more DHE staining (40.3±2.9 FU/HPF) than HF diet (28.3±2.9 FU/HPF) and chow fed mice (17±1.0 FU/HPF) (p=0.002) (FIGS. 5A-5C).

Quantification of CoQ9 was performed using a previously published method (Tang P H et al., Measurement of reduced and oxidized coenzyme Q9 and coenzyme Q10 levels in mouse tissues by HPLC with coulometric detection. Clin Chim Acta 2004; 341:173-184). Frozen plasma with internal standard CoQ11 was injected into an automated high-performance liquid chromatographic (HPLC) system equipped with a coulometer detector. Quantification of $_{ox}$CoQ9 was obtained by the CHROMQUEST™ software (Fisher Scientific, Pittsburgh, Pa.). After injection, the extract was mixed with 1,4-benzoquinone, incubated and then injected into the HPLC system for measuring total CoQ9. Concentration of reduced coenzyme Q9 was achieved by subtracting $_{ox}$CoQ9 from total CoQ9.

Figure 5E:
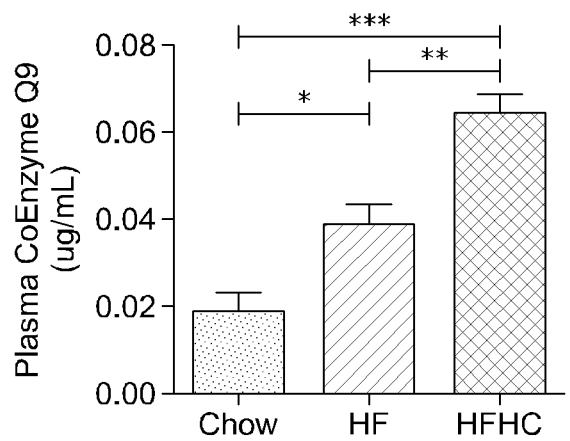

The correlation of liver tissue collagen 1 mRNA relative expression and absolute plasma $_{ox}$CoQ9 levels had an $R^2$ value of 0.51. HFHC and HF diet fed mice had higher $_{ox}$CoQ9 plasma levels than chow fed mice (1 way ANOVA; p<0.0001). For example, plasma $_{ox}$CoQ9 levels in mice at 16 weeks were significantly higher in HFHC fed mice (0.06±0.004 μg/mL) than HF diet fed mice (0.03±0.004 μg/mL) and chow diet fed mice (0.02±0.004 μg/mL) (p<0.0001) (Table 2 and FIG. 5E). HFHC diet fed mice also had significantly increased plasma total CoQ9 levels compared to both HF and chow fed mice after 16 weeks of diet (1 way ANOVA; p=0.0141). Thus, the fructose-containing HFHC diet had the most hepatic ROS and fibrosis. This was mirrored by the levels of plasma $_{ox}$CoQ9, which differed significantly among all three groups.

TABLE 2

Plasma CoEnzyme Q9 Profile after 16 weeks of Diet

| Parameters | Chow | HF | HFHC |
|---|---|---|---|
| $_{red}$Q9 (µg/mL) | 0.1204 ± 0.03 | 0.2318 ± 0.04 | 0.2518 ± 0.04 |
| $_{ox}$Q9 (µg/mL) | 0.019 ± 0.004 | 0.0388 ± 0.004* | 0.064 ± 0.005***## |
| $_{tot}$Q9 (µg/mL) | 0.1394 ± 0.03 | 0.2706 ± 0.05 | 0.3158 ± 0.03* |
| $_{red}$Q9/$_{ox}$Q9 Ratio (AU) | 6.825 ± 1.2 | 5.846 ± 0.8 | 4.161 ± 0.8 |

Tukey's post test
***= p < 0.001,
= p < 0.01,
*= p < 0.05
*= versus chow,
= versus HF
N for groups: chow = 5; HF = 5, HFHC = 5

Example 7

Cross-Sectional Study for Fatty Liver Disease (FLD)

A cross-sectional study was conducted for 54 extremely obese adolescents with clinical liver biopsies performed at time of bariatric surgery. Stored serum and liver histology data were obtained from an Obesity Tissue Repository (OTR) of prospectively collected baseline liver tissue, fasting serum, and associated clinical data in adolescents undergoing bariatric surgery at CCHMC. Subjects were recruited from patients undergoing bariatric surgery in the Surgical Weight Loss Program for Teens (SWLPT) at CCHMC. The age range of subjects was 13 to 29 years.

The histologic phenotype of liver disease in each subject was graded and scored using standardized validated methods (Kleiner D E et al., Design and validation of a histological scoring system for nonalcoholic fatty liver disease. *Hepatology* 2005; 41:1313-21). Patients were classified into four groups based on liver histology: 1) normal; 2) hepatic steatosis only; 3) indeterminate NAFLD (steatosis+inflammation, but not meeting criteria for NASH); and 4) NASH(NAS activity score of ≥3 with fibrosis) (Table 3).

TABLE 3

Patient Population

| Stage of Liver Disease | # of Patients |
|---|---|
| Normal | 4 |
| Not Fatty Liver Disease | 15 |
| Steatosis Only | 8 |
| Steatosis + Inflammation | 12 |
| NASH | 15 |
| Total | 54 |

Serum levels of CoQ10$_{ox}$, CoQ10$_{red}$ and total CoQ10 were measured using well-validated techniques (Miles M V et al., Age-related changes in plasma coenzyme Q10 concentrations and redox state in apparently healthy children and adults. *Clin Chim Acta* 2004; 347:139-44). CoQ levels were measured for differences across disease groups compared with a No FLD control group (normal and Not FLD samples). Due to extreme points that may skew the mean, all analyses were conducted using the nonparametric Kruskal-Wallis (KW) approach. Because the level of triglycerides (TG), cholesterol, and LDL cholesterol can affect serum CoQ levels, the raw data was adjusted by dividing CoQ by TG, LDL, total cholesterol (TC), and TG+TC. To determine if there was a significant difference in CoQ levels between normal vs. all fatty liver disease groups combined, the two independent sample t-test was conducted at the 5% two-sided level of significance. All tests were conducted at the 5% two-sided level of significance.

Figure 6A:
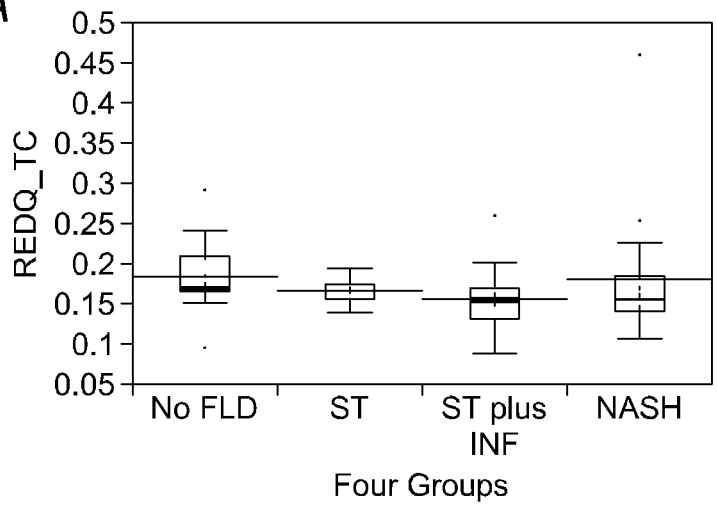
FIG. 6 shows median reduced Coenzyme Q (CoQ) levels when adjusted for low-density lipoprotein (LDL) levels in normal patients and patients without fatty liver disease (Not FLD), patients with steatosis only (ST), patients with indeterminate NASH without fibrosis (i.e., steatosis and inflammation) (ST plus INF), and patients with NASH with fibrosis (NASH) (FIG. 6A); and median reduced CoQ levels adjusted for total cholesterol (TC) in patients with No FLD (normal and Not FLD samples), ST, ST plus INF, and NASH (FIG. 6B). Horizontal lines within the boxes indicate median values. Horizontal lines running through the boxes indicate mean values. Points outside the bars of the boxes are outliers.
Figure 6B:
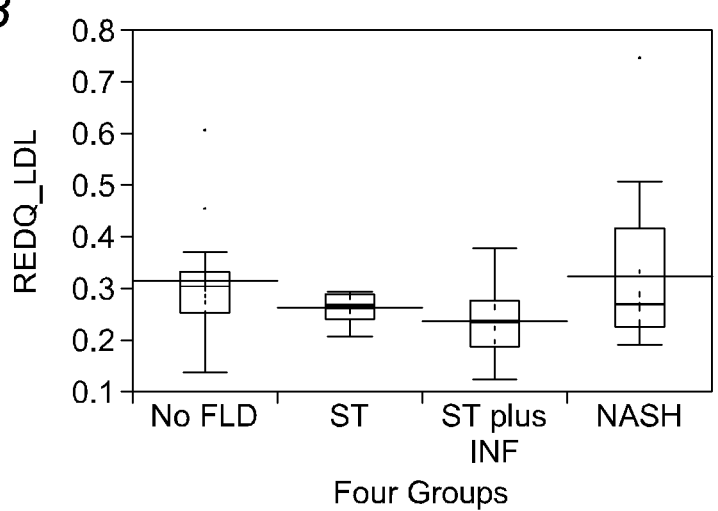

Median reduced CoQ adjusted for LDL levels was significantly higher in the No FLD control group than the three fatty liver disease groups (FIG. 6B). Pairwise comparisons resulted in the following p values: No FLD vs. ST: p=0.0495; No FLD vs. ST plus INF: p=0.01; No FLD vs. NASH: p=0.11; ST vs. ST plus INF: p=0.19; ST vs. NASH: p=0.8; and ST plus INF vs. NASH: p=0.11 (FIG. 6B; KW p-value=0.0472). When reduced CoQ was adjusted for total cholesterol, this approached a level of significance (FIG. 6A; KW p-value=0.09).

Figure 7A:
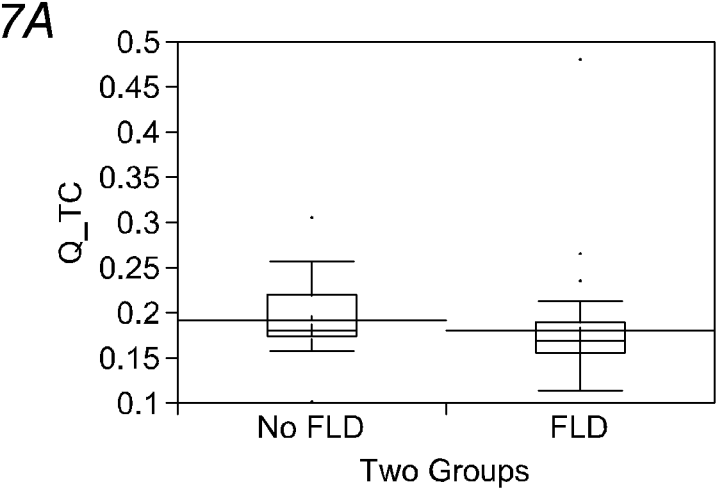
FIG. 7 shows median total CoQ levels in patients with No FLD (normal and Not FLD samples) or FLD when adjusted for TC (FIG. 7A), LDL (FIG. 7B), and triglycerides (TCTG) (FIG. 7C); and median reduced CoQ levels in patients with No FLD or FLD when adjusted for TC (FIG. 7D), LDL (FIG. 7E), trigylcerides (TG) (FIG. 7F), TG (FIG. 7F), and TCTG (FIG. 7G). Horizontal lines within the boxes indicate median values. Horizontal lines running through the boxes indicate mean values. Points outside the bars of the boxes are outliers.
Figure 7B:
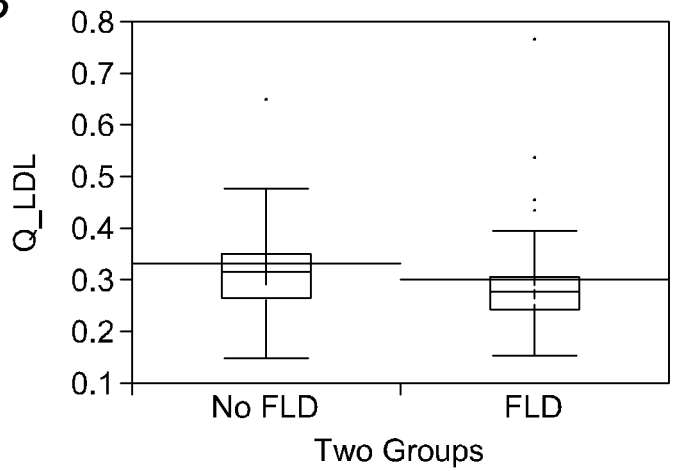
Figure 7C:
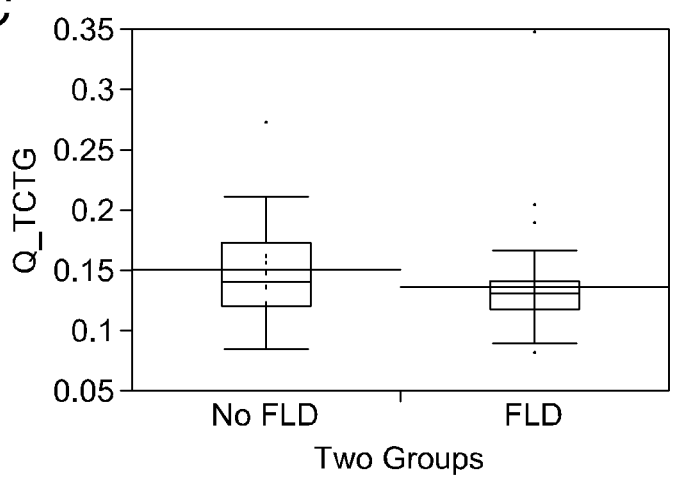
Figure 7D:
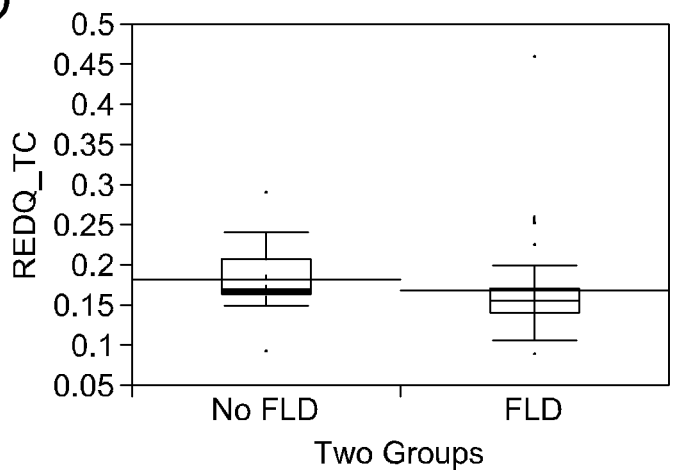
Figure 7E:
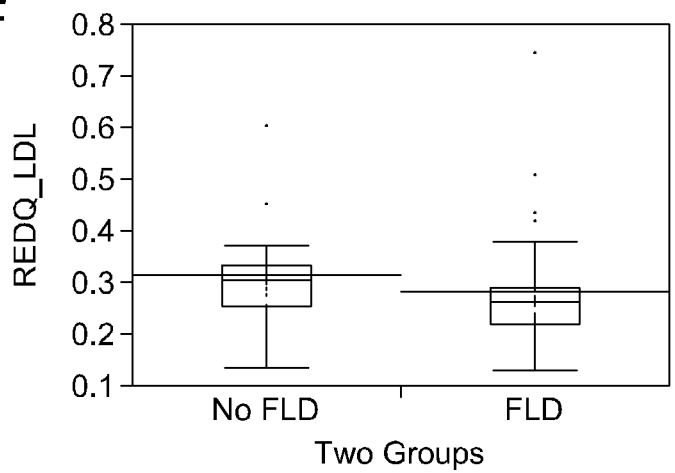
Figure 7F:
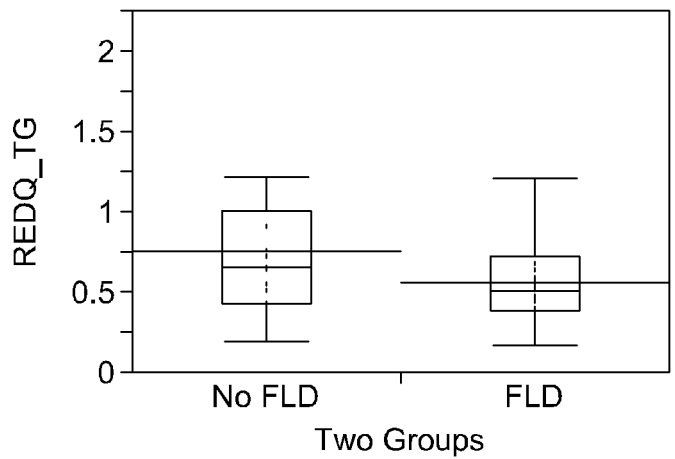
Figure 7G:
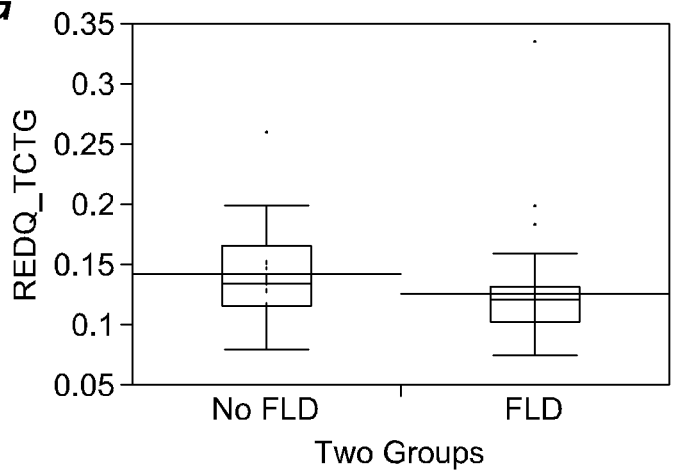

Median total CoQ levels adjusted for total cholesterol (FIG. 7A; KW p-value=0.03) and LDL (FIG. 7B; KW p-value=0.03) were significantly lower in fatty liver disease than the No FLD control group. Median reduced CoQ levels adjusted for TC (FIG. 7D; KW p-value=0.02), LDL (FIG. 7E; KW p-value=0.02), and TC+TG (FIG. 7G; KW p-value=0.04) were significantly lower in fatty liver disease than the No FLD control group. Median reduced CoQ levels adjusted for TG+TC (FIG. 7c; KW p-value=0.08) and TG (FIG. 7F; KW p-value=0.09) were also lower in fatty liver disease than the No FLD control group.

These data indicate that total CoQ and reduced CoQ levels are significantly reduced in NAFLD compared to controls, and that reduced CoQ can serve as a marker for fatty liver disease.

Example 8

Receiver Operating Characteristic (ROC) Analysis

Receiver operating characteristic (ROC) analysis is widely accepted as a preferred method for characterizing and comparing the overall diagnostic accuracy and validity of laboratory tests or diagnostic measures because it incorporates the trade-off between sensitivity and specificity over the range of that test. In addition, by maximizing the sum of the sensitivity and the specificity of a test, ROC analysis can provide a preferred threshold or cutpoint for a test or model.

ROC analysis parameters were calculated for reduced, oxidized, and total coenzyme Q10 (adjusted for lipoproteins, including TC, LDL, HDL, TG, and TG+TC) and reduced: total CoQ10 ratio based on the likely presence or absence of fatty liver disease. Table 4 provides a summary of ROC analyses performed for the data generated in Example 7. ROC analyses generating the lowest p values are indicated in bold text.

TABLE 4

ROC Analysis of Human Data

| CoQ10 Measure | Sensitivity (%) | Specificity (%) | Area under the ROC Curve | Significance Level | Cutpoint Value (μmol CoQ/ mmol lipid) |
|---|---|---|---|---|---|
| Reduced CoQ10 | | | | | |
| Adjusted for TC | 71.4 | 68.4 | 0.698 | 0.008 | <0.170 |
| Adjusted for LDL | 80.0 | 63.2 | 0.690 | 0.012 | ≤0.293 |
| Adjusted for TC + TG | 80.0 | 63.2 | 0.674 | 0.034 | ≤0.131 |
| Adjusted for TG | 68.6 | 57.9 | 0.642 | 0.088 | ≤0.630 |
| Adjusted for HDL | 77.1 | 42.1 | 0.546 | 0.585 | >0.639 |
| Total CoQ10 | | | | | |
| Adjusted for TC | 62.9 | 79.0 | 0.681 | 0.017 | <0.176 |
| Adjusted for LDL | 80.0 | 63.2 | 0.680 | 0.021 | <0.307 |
| Adjusted for TC + TG | 77.1 | 57.9 | 0.645 | 0.086 | ≤0.142 |
| Adjusted for TG | 94.29 | 31.58 | 0.624 | 0.140 | ≤0.920 |
| Adjusted for HDL | 77.14 | 42.11 | 0.564 | 0.447 | >0.678 |
| Oxidized CoQ10 | | | | | |
| Adjusted for TC | 17.14 | 100.0 | 0.503 | 0.970 | >0.016 |
| Adjusted for LDL | 42.9 | 73.4 | 0.511 | 0.893 | ≤0.015 |
| Adjusted for TC + TG | 34.29 | 89.47 | 0.526 | 0.743 | ≤0.006 |
| Adjusted for TG | 85.71 | 31.58 | 0.555 | 0.516 | ≤0.051 |
| Adjusted for HDL | 48.6 | 89.5 | 0.618 | 0.123 | >0.051 |
| REDOX Status for CoQ10 | | | | | |
| Reduced: Total CoQ | 34.3 | 94.7 | 0.537 | 0.665 | ≤0.935 |

Example 9

Cross-Sectional Study for Staging of Fatty Liver Disease

A cross-sectional study is performed as described in Example 7 in a larger cohort of non-bariatric adolescents with biopsy proven NASH. Levels of total CoQ, reduced CoQ, and oxidized CoQ are investigated to discriminate between steatosis, steatosis with inflammation, and fibrotic NASH.

Example 10

Cross-Sectional Study for Staging of Fatty Liver Disease

A cross-sectional study is performed as described in Example 7 in a larger cohort of adults with biopsy proven NASH. Levels of total CoQ, reduced CoQ, and oxidized CoQ are investigated to discriminate between steatosis, steatosis with inflammation, and fibrotic NASH.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method of determining the presence of fatty liver disease (FLD) in a patient, comprising:
   providing a sample from a patient;
   measuring the level of coenzyme Q (CoQ) in the sample; and
   comparing the CoQ value from the patient with a threshold value, wherein if the CoQ value meets the threshold value the patient is determined to be at risk for fatty liver disease.

2. The method of claim 1, wherein the CoQ measurement is a measurement of reduced CoQ.

3. The method of claim 1, wherein the CoQ measurement is a measurement of total CoQ.

4. The method of claim 1, wherein the CoQ measurement is a measurement of oxidized CoQ.

5. The method of claim 1, wherein the CoQ measurement is a measurement of coenzyme Q10 (CoQ10).

6. The method of claim 1, wherein the CoQ measurement is the ratio of reduced CoQ10:total CoQ10.

7. The method of claim 1, wherein the sample is selected from the group consisting of blood, plasma, serum, or a tissue.

8. The method of claim 7, wherein the sample is plasma.

9. The method of claim 1, wherein the threshold value is determined using a value calculated using a receiver operating characteristic (ROC) analysis.

10. The method of claim 2, further comprising adjusting the measurement of reduced CoQ based on a lipid level in the sample to form an adjusted CoQ value.

11. The method of claim 10, wherein the measurement of reduced CoQ is adjusted for the total cholesterol level in the sample.

12. The method of claim 11, wherein the threshold value is a median reduced CoQ of less than about 0.17 μmol CoQ10/mmol lipid.

13. The method of claim 10, wherein the measurement of reduced CoQ is adjusted for the low-density lipoprotein (LDL) level in the sample.

14. The method of claim 13, wherein the threshold value is a median reduced CoQ of less than about 0.293 μmol CoQ10/mmol lipid.

15. The method of claim 10, wherein the measurement of reduced CoQ is adjusted for the triglyceride level in the sample.

16. The method of claim 15, wherein the threshold value is a median reduced CoQ of less than about 0.63 μmol CoQ10/mmol lipid.

17. The method of claim 10, wherein the measurement of reduced CoQ is adjusted for the total cholesterol level and the triglyceride level in the sample.

18. The method of claim 17, wherein the threshold value is a median reduced CoQ of less than about 0.131 μmol CoQ10/mmol lipid.

19. The method of claim 10, wherein the measurement of reduced CoQ is adjusted for the high-density lipoprotein (HDL) level in the sample.

20. The method of claim 19, wherein the threshold value is a median reduced CoQ of more than about 0.639 μmol of CoQ10/mmol lipid.

21. The method of claim 3, further comprising adjusting the measurement of total CoQ based on a lipid level in the sample to form an adjusted CoQ value.

22. The method of claim 21, wherein the measurement of total CoQ is adjusted for the total cholesterol level in the sample.

23. The method of claim 22, wherein the threshold value is a median total CoQ of less than about 0.176 μmol CoQ10/mmol lipid.

24. The method of claim 21, wherein the measurement of total CoQ is adjusted for the low-density lipoprotein (LDL) level in the sample.

25. The method of claim 24, wherein the threshold value is a median total CoQ of less than about 0.307 μmol CoQ10/mmol lipid.

26. The method of claim 21, wherein the measurement of total CoQ is adjusted for the triglyceride level in the sample.

27. The method of claim 26, wherein the threshold value is a median total CoQ of less than about 0.92 μmol CoQ10/mmol lipid.

28. The method of claim 21, wherein the measurement of total CoQ is adjusted for the total cholesterol level and the triglyceride level in the sample.

29. The method of claim 28, wherein the threshold value is a median total CoQ of less than about 0.142 μmol CoQ10/mmol lipid.

30. The method of claim 21, wherein the measurement of total CoQ is adjusted for the high-density lipoprotein (HDL) level in the sample.

31. The method of claim 30, wherein the threshold value is a median total CoQ of more than about 0.678 μmol CoQ10/mmol lipid.

32. The method of claim 4, further comprising adjusting the measurement of oxidized CoQ based on a lipid level in the sample to form an adjusted CoQ value.

33. The method of claim 32, wherein the measurement of oxidized CoQ is adjusted for the total cholesterol level in the sample.

34. The method of claim 33, wherein the threshold value is a median oxidized CoQ of less than about 0.016 μmol CoQ10/mmol lipid.

35. The method of claim 32, wherein the measurement of oxidized CoQ is adjusted for the low-density lipoprotein (LDL) level in the sample.

36. The method of claim 35, wherein the threshold value is a median oxidized CoQ of less than about 0.015 μmol CoQ10/mmol lipid.

37. The method of claim 32, wherein the measurement of oxidized CoQ is adjusted for the triglyceride level in the sample.

38. The method of claim 37, wherein the threshold value is a median oxidized CoQ of less than about 0.051 μmol CoQ10/mmol lipid.

39. The method of claim 32, wherein the measurement of oxidized CoQ is adjusted for the total cholesterol level and the triglyceride level in the sample.

40. The method of claim 39, wherein the threshold value is a median oxidized CoQ of less than about 0.006 μmol CoQ10/mmol lipid.

41. The method of claim 32, wherein the measurement of oxidized CoQ is adjusted for the high-density lipoprotein (HDL) level in the sample.

42. The method of claim 41, wherein the threshold value is a median oxidized CoQ of more than about 0.051 μmol of oxidized CoQ10/mmol lipid.

43. The method of claim 6, wherein the ratio of reduced CoQ10:total CoQ10 is less than about 0.935.

44. The method of claim 1, further comprising determining the stage of FLD in the patient.

45. The method of claim 44, wherein the stage of FLD is nonalcoholic fatty liver disease (NAFLD).

46. The method of claim 44, wherein the stage of FLD is nonalcoholic steatohepatitis (NASH).

47. The method of claim 46, further comprising determining the stage of fibrosis in NASH in the patient.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Homo sapiens
<220> FEATURE:
<221> NAME/KEY: misc_feature
<222> LOCATION: (0)...(0)
<223> OTHER INFORMATION: reverse primer sequence

<400> SEQUENCE: 1
cgtagtagac gatgggcagt gg                                            22

<210> SEQ ID NO 2
<211> LENGTH: 22
<212> TYPE: DNA
<213> ORGANISM: Homo sapiens
```

-continued

```
<220> FEATURE:
<221> NAME/KEY: misc_feature
<222> LOCATION: (0)...(0)
<223> OTHER INFORMATION: forward primer sequence

<400> SEQUENCE: 2
tatttggagc ctggacacac ag                                              22
```